United States Patent [19]

Kiplinger

[11] Patent Number: 5,500,369

[45] Date of Patent: Mar. 19, 1996

[54] AIR SAMPLER

[75] Inventor: Dale V. Kiplinger, Carrollton, Tex.

[73] Assignee: NCH Corporation, Irving, Tex.

[21] Appl. No.: 135,793

[22] Filed: Oct. 12, 1993

[51] Int. Cl.$^6$ .............................. G01N 5/02; G01F 1/68; C12M 1/26; C12M 1/00

[52] U.S. Cl. .................. 435/309.1; 73/31.01; 73/31.02; 73/204.21; 73/861.63; 73/863; 73/863.12; 73/863.22; 73/863.33; 73/863.41; 73/863.43; 73/864; 73/864.71; 435/283.1

[58] Field of Search .............................. 15/344; 435/287, 435/299, 313, 292, 294, 300, 301, 309, 314; 73/31.01, 31.02, 31.03, 204.21, 861.63, 863, 863.12, 863.22, 863.33, 863.41, 863.43, 864, 864.71

[56] References Cited

U.S. PATENT DOCUMENTS

| | | | |
|---|---|---|---|
| 3,127,329 | 3/1964 | Anderson | 195/103.5 |
| 3,576,721 | 4/1971 | Mason | 195/139 |
| 3,684,660 | 8/1972 | Kereluk et al. | 195/139 |
| 3,795,135 | 3/1974 | Anderson | 73/28 |
| 3,922,905 | 12/1975 | Roth | 73/28 |
| 3,968,012 | 7/1976 | Jones | 195/142 |
| 3,972,226 | 8/1976 | Rountree et al. | 73/28 |
| 3,980,524 | 9/1976 | Reuter | 195/139 |
| 4,038,057 | 7/1977 | Roth | 55/270 |
| 4,209,875 | 7/1980 | Pugh et al. | 15/344 |
| 4,663,293 | 5/1987 | Hempel et al. | 435/294 |
| 5,201,231 | 4/1993 | Smith | 73/863.22 |

Primary Examiner—Michael G. Wityshyn
Assistant Examiner—Jane Williams
Attorney, Agent, or Firm—Dennis T. Griggs

[57] ABSTRACT

A hand-held portable sampler uses a vacuum to induce the flow of air into an air chamber and around a deflector plate mounted substantially transverse to the overall airflow pattern and with edges thereof close to the surface of nutrient material contained in culture containers between opposite sides of the enclosure and the deflector plate to define a constricted air passage. Particulates in the air are caused to impact the surface of nutrient material contained in culture containers as air is deflected through the constricted area. The venturi effect of the constricted area causes turbulence downstream to continue the process of impacting particulates in the nutrient material downstream from the constricted area of the air deflector.

6 Claims, 4 Drawing Sheets

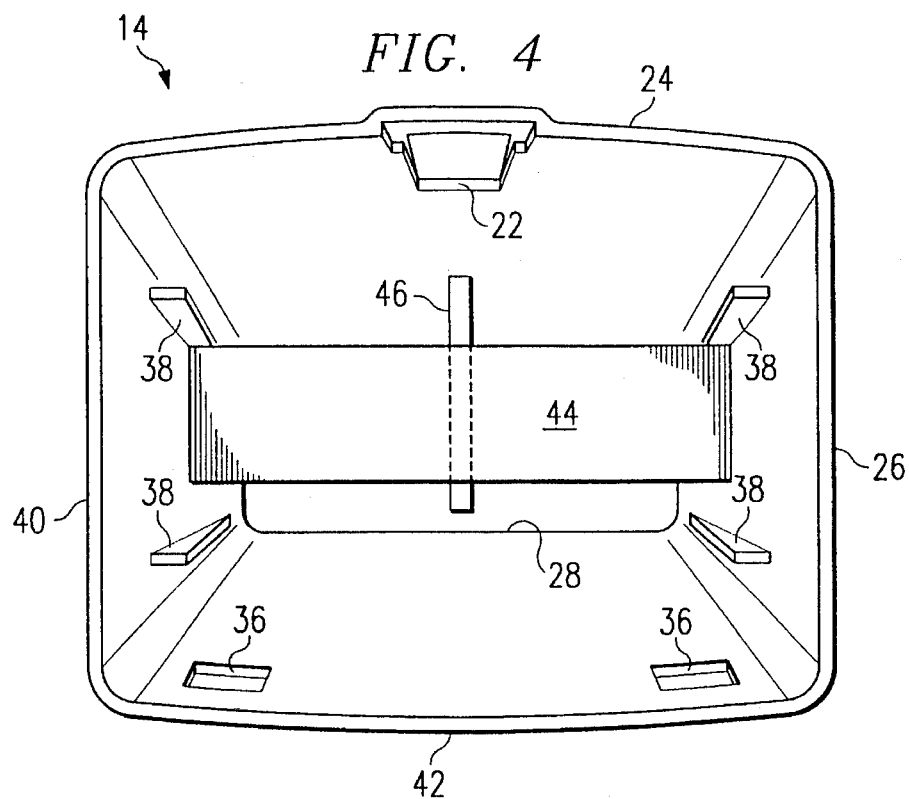
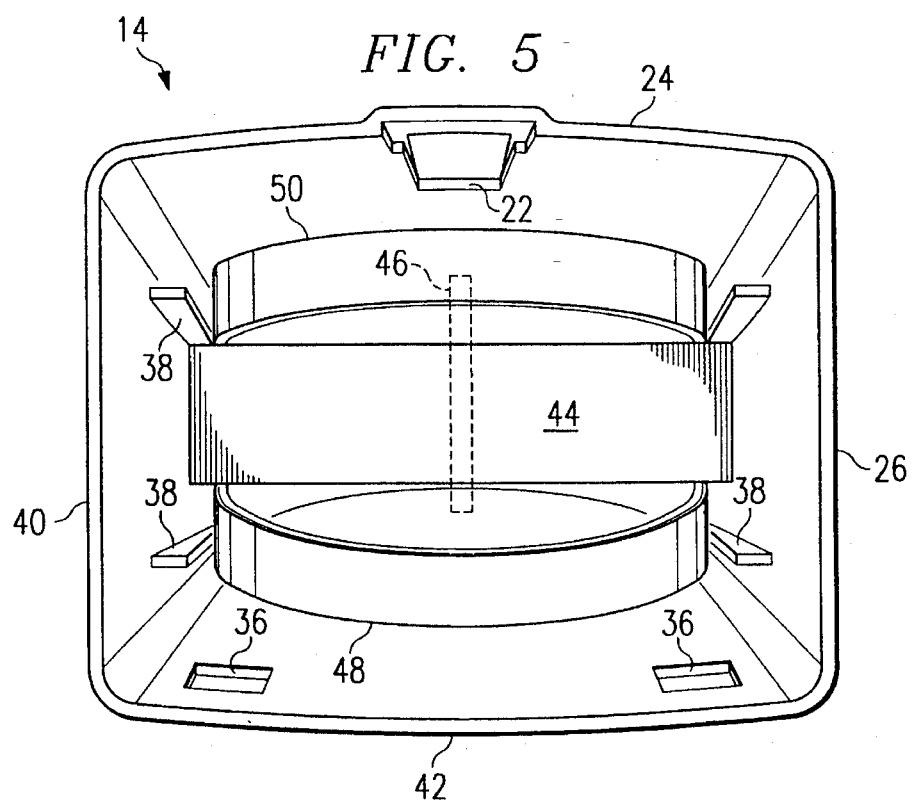

AIR SAMPLER

FIELD OF THE INVENTION

This invention is related generally to respirable gaseous medium sampling devices and more particularly to portable respirable gaseous medium sampling devices wherein culture dishes used therewith may be quickly and easily replaced to facilitate obtaining distinct and separate respirable gaseous medium sample cultures from different areas of a room or from different rooms or surfaces.

BACKGROUND OF THE INVENTION

There is always a concern over the presence of particulate contaminates, especially viable particulate contaminates, in a respirable gaseous medium such as air. The need for constant atmospheric and surface surveillance is apparent in connection with the manufacturing and packaging of medicines, pharmaceutical and the like, food processing plants, in hospitals and other institutions where the aged and/or infirm are present, and in situations where strict hygienic conditions are to be maintained. The detection of airborne micro-organisms as part of this surveillance is often of decisive significance in human and veterinary medicine as well as in the pharmaceutical and food industries. Conventional devices are available for testing air and surfaces such as carpets, hard floors, ceiling tiles, desks, sinks and other areas where micro-organisms are found. They function in accordance with various principles, are operated in accordance with different methods, and yield differing results, both qualitatively and quantitatively.

Carpets, furniture and air ducts are major sources of airborne micro-organisms. Furthermore, effective treatment of those sources by use of disinfecting chemicals and routine cleaning can reduce the population of airborne colonies. Treatment of air ducts and filters can be demonstrated by quantitive measurement of the source and effectiveness of the treatments. This can be done by either sampling from the surface or measuring the effects within the free air.

Measurement and treatment of carpets and other surfaces may reduce illness in areas such as daycare centers, schools and nursing homes where contageous illnesses may be spread. Concerns over sick building syndrome create a demand for surveillance of closed buildings which lack fresh air input, including source identification, measurement and treatment.

Many prior art testing devices perform quantitative and qualitative analyses of contaminates in the ambient atmosphere. However, the test results have often been inconsistent. This is often due to the common assumption typically employed in testing gaseous volumes that germs or other contaminates collected by the testing devices are equally distributed in the atmosphere. In other words, this assumption has been proven to be invalid. Thus, a test of a small portion, as an example, a cubic meter of the gaseous medium such as the atmosphere in a large room for colony forming bacteria will not provide a basis for determining, with any degree of accuracy, the bacteria content of the entire room. It is thus apparent that testing devices should be designed to selectively and specifically test the air for contaminates in different areas of a given room so that the source of the contaminates can more easily be ascertained. A hand held portable device can offer a means to readily sample a cross section or average condition of a room or surface.

DESCRIPTION OF THE PRIOR ART

Some of the prior art devices operate on the centrifuge principle. For the most part, centrifugal-type air samplers are used to determine the mass, size and nature of both the viable and non-viable particulates constituting the contamination. Generally, such air sampling devices require external electric power and their weight makes them difficult to handle and transport. Further, there is difficulty keeping them sterile as a result of their size and complexity.

Conventional hand-held air samplers have utilized an impeller to both draw in contaminated air and to cause the contaminates to be impacted against the culture medium. In other words, the impellers are in the upstream air and can affect the accuracy of air samples taken at a later time unless the device is completely sterilized between air sample attempts. As will be realized, the sterilization of curved surfaces, such as occur in connection with impeller blades, is often difficult to accomplish without the emersion of the curved surfaces in a sterilizing liquid or the application of steam to the device.

Some respirable gaseous medium sampling devices draw in a gas such as air with a rapidly rotating impeller located in an air channeling cylinder. This impeller causes the air to be directed against an axially parallel layer of a culture medium. The rotating impeller will typically become contaminated from particulates in the air which may affect the results of testing in other areas. Some prior art sampling device designers believe that the amount of particulates causing this contamination may be minimized by positioning the blades of such an impeller at between 15° and 40° with respect to the plane in which it rotates. However, for utmost accuracy, the impeller blade still should be cleaned between each air sample test attempt. Further air channeling is utilized in such devices to precipitate smaller micro-organisms. The channeling supposedly causes the air to flow non-turbulently through an annular chamber between the outer surface of the cylinder and a backing sheet containing culture medium.

Another type of respirable gaseous medium sampling device employs the approach or concept of jet impaction of airborne particulates to separate these particles into classes. Typically, such a device includes multiple stages which are serially arranged and in which the velocity of the gaseous medium being sampled as it impinges against the collecting medium is increased through successive stages. One limitation on the use of these prior art air sampling devices is that they have been relatively expensive to manufacture to the precision tolerances required for successful operation.

Further, difficulty has been encountered in the regulation of the flow rate of the gaseous medium through such sampling devices since the classification of the airborne particles is dependent upon the velocity of the gaseous medium passing through the sampler. The multiple openings creating the jets of necessity become contaminated, consequently the entire sampling device should be sterilized between each sampling operation to prevent false readings on subsequent operations. Attempts to minimize the contamination problem have resulted in devices which comprise a culture medium encased in a throw-away housing containing the various jets and the entire throw-away container is inserted into a vacuum inducing device. Although the entire throw-away container may be at times constructed of plastic, there is still considerable expense and wastage for each sample.

OBJECTS OF THE INVENTION

The principal object of the present invention is to provide a device that will provide sampling of contamination of the air or other media such as hard surfaces, carpets, upholstery, etc. to locate and effectively show effects of treatments of these media.

A related object of the present invention is to provide an improved portable design of a respirable gaseous medium or air sampler.

Another object of the present invention is to provide a portable air sampler which uses standard culture dishes for containing the nutrient media.

A further object of the present invention is to remove the air handling or air moving device to the downstream side of the nutrient media so that the air handler does not contribute to contamination of successively taken air samples.

Another object of the present invention is to minimize the dexterity required of the operator to replace culture dishes containing nutrient media between air samples.

A related object of the present invention is to minimize replacement time for changing culture dishes between air samples in a portable air sampler.

Yet another object is to provide an improved air sampler which minimizes the probability that the taking of a given air sample will cause contamination and/or affect the accuracy of later taken air samples.

A further object of the invention is to provide an improved method of managing air flow to cause impregnation of culture media by particulates and micro-organisms contained in the air being sampled.

Another object of the present invention is to provide an improved air sampler having a housing which can be easily disassembled for sterilization in the unlikely event that the device has become so contaminated that it affects the accuracy of later taken samples.

Still another object of the invention is to provide a selective media sampling technique where two different media can simultaneously measure the same air stream and selective cultures of bacteria and fungi can be cultured and measured.

SUMMARY OF THE INVENTION

The foregoing objects are achieved by the present invention in a hand-held sampling device which includes a nose portion, a suction fan and a tail portion which is easily detachable from a nose portion. The nose portion includes an aerodynamic deflector of air or other respirable gaseous medium and at least one nutrient media container on an inside surface of the nose. When the nose is attached to the tail, the nutrient media container(s) is held firmly in place and upon activation of the fan, air is drawn into the nose piece. The air deflector and the nutrient media in the container create a constricted cross-sectional area air gap. The air gap creates a venturi effect which generates turbulence downstream from the gap. This gap and the transverse deflection of the air within the nose and the subsequent turbulence causes impaction of microscopic particles into the nutrient media even though the general overall air path is parallel to the surface of the nutrient media.

In the preferred embodiment, two nutrient media containers are typically used, on opposite sides of an air deflector, so as to detect different types of organisms if appropriate upon selective media such as one specific to bacteria and another specific to fungi and molds. Since the nose piece is easily detachable, the nutrient media containers can be easily removed and new ones inserted so that air samples can be taken in a different area of the room. Further, since the air being sampled is almost immediately passed over the nutrient media after being brought into the sampling device and the nutrient media is upstream from the fan, there is no contamination of the air or detrimental effects on the micro-organisms by the fan impellers which might affect later air samples.

If the environment is such that the nose of the air sampler should be sterilized between uses, the nose design is readily adaptable to being taken apart and cleaned either by hand or spraying with an aerosol disinfectant or pump sprayer, or by dipping in a liquid solution.

Operational features and advantages of the present invention will be understood by those skilled in the art upon reading the detailed description which follows with reference to the attached drawings.

BRIEF DESCRIPTION OF THE DRAWINGS

FIG. 4 is an end view of the nose piece showing the air deflector plate and a air divider/culture dish or container stop;

FIG. 5 is an end view similar to FIG. 4 with two culture dishes inserted between the top and bottom of the housing and the deflector plate and held in place by constraining ribs;

DETAILED DESCRIPTION OF THE PREFERRED EMBODIMENT

Figure 1:
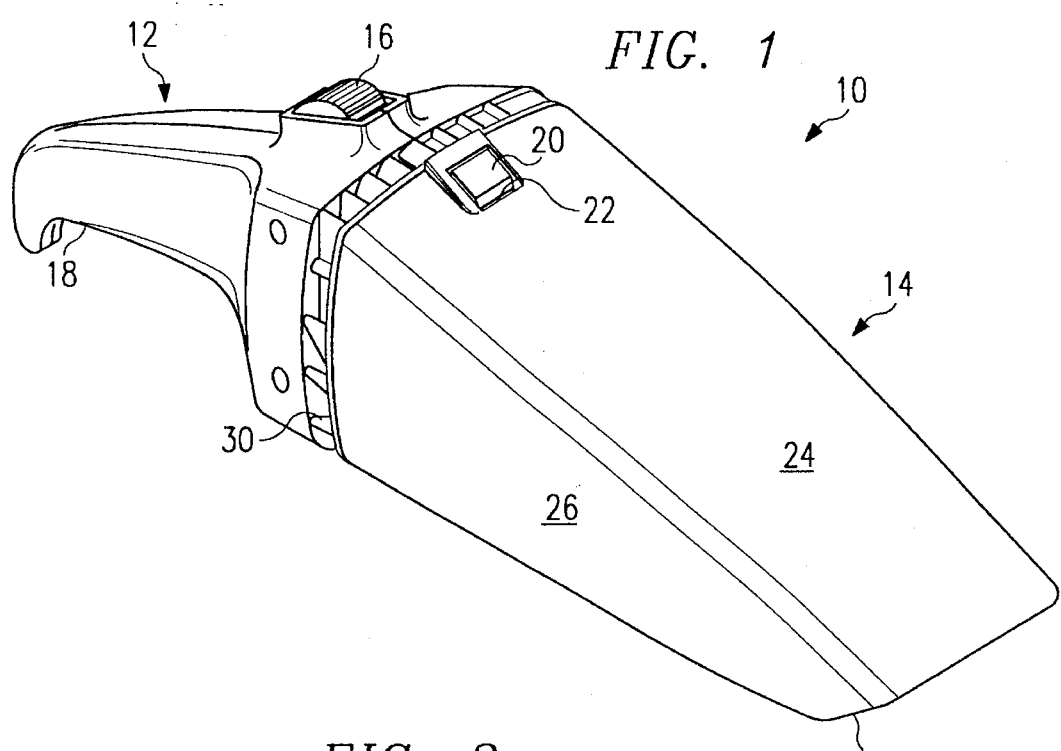
FIG. 1 is a perspective view of the vacuum sampler in a closed or attached condition.

In FIG. 1, a portable vacuum sampler 10 is shown with a tail portion 12 and nose portion 14. Tail portion 12 includes an electrical switch 16 in a handle 18. The switch 16 serves to actuate an electric motor and associated fan in the tail portion 12 but not shown in FIG. 1. The nose piece 14 includes an opening 22 through which a detent button 20, comprising a portion of tail 12, extends. By depressing button 20, nose 14 is allowed to become detached from tail 12. A top portion of nose 14 is labeled 24 while a side portion is labeled 26. An air inlet nozzle for nose 14 is labeled 28. Air outlets for the sampler are located in tail 12. Some of these openings are designated as 30.

In the following drawings, like parts are indicated throughout the specification and drawings with the same reference numerals as used in previous drawings. The drawings are not necessarily to scale and the proportions of certain parts may have been exaggerated to better illustrate details of the present invention.

Figure 2:
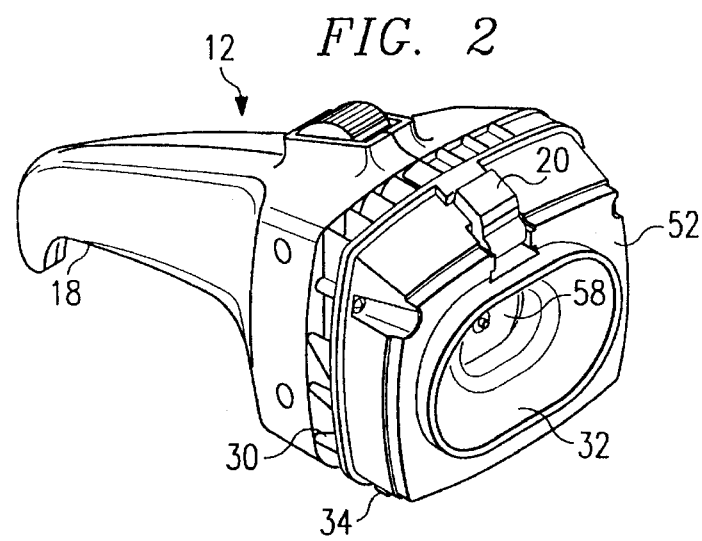
FIG. 2 is a perspective view of the tail portion of the vacuum sampler which includes the vacuum inducing fan and motor and actuating switch.

As shown in FIG. 2, the tail portion 12 has an air inlet 32 which directs air into a motor driven fan 58 and the air exits through the exit vents 30. Also shown in FIG. 2 is one of two assembly projections 34 in the tail which interact with corresponding openings 36 in the nose as illustrated in FIG. 3.

Figure 3:
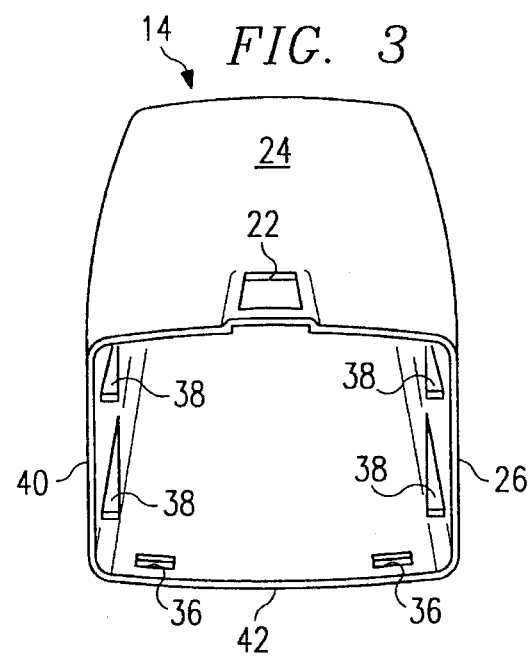
FIG. 3 is a perspective view of the nose portion disassembled from the tail portion and looking into the air outlet portion of the nose section.

FIG. 3 shows in addition to the two sides 24 and 26, that the air flow housing of FIG. 3 additionally has a further side 40 opposite side 26 and a bottom portion 42. Internal to the air housing of nose 14 are positioning or nutrient media container constraining ribs 38. As will be apparent from FIGS. 1–3, the parts of FIGS. 2 and 3 can be assembled to provide the vacuum sampler of FIG. 1 by inserting projections 34 (only one of which is shown in FIG. 2) into the two openings 36 of FIG. 3 and then tilting the nose piece in an upward direction such that quick release button 20 is depressed until it is coincident with opening 22 at which time it is forced outward by spring means (not specifically designated) to maintain the nose 14 in a attached condition to tail 12. The vacuum sampler can be easily disassembled by depressing button 20 against the spring force and tilting the nose 14 in a downward direction until it is tilted far enough that the entire nose assembly 14 can be moved downwardly with respect to tail 12 and detach the projections 34 from the openings 36.

In FIG. 4 it will be apparent that there is a space or gap between an aerodynamic deflector plate 44 and the upper or top portion 24 of the air flow housing comprising nose 14. There is also a gap or space between the bottom of deflector plate 44 and the bottom portion 42 of the air flow housing comprising nose 14. As may be further observed from the dashed lines, an air divider and culture container stop 14 is placed intermediate deflector plate 44 and the air inlet nozzle 28 of nose 14.

FIG. 5 illustrates the nose 14 from the same viewpoint as is shown in FIG. 4 with culture or nutrient media containers, petri dishes or culture dishes 48 and 50 inserted into position with a snug fit between positioning ribs 38. These culture dishes are slid forward until they rest against the air divider 46 which also serves as a container stop. When the tail 12 is assembled with the nose 14, the front portion of air inlet 32 serves as a rear stop to retain the culture dishes 48 and 50 in position. Thus, in addition to the container movement constraining pressure exhibited by the ribs 38, the combination of the air divider 46 and the front portion of air inlet 32 prevents any substantial container movement forward or backward and the containers are further prevented from any substantial movement up and down by the deflector plate 44 and the top and bottom portions of the air flow housing of nose 14.

Figure 6:
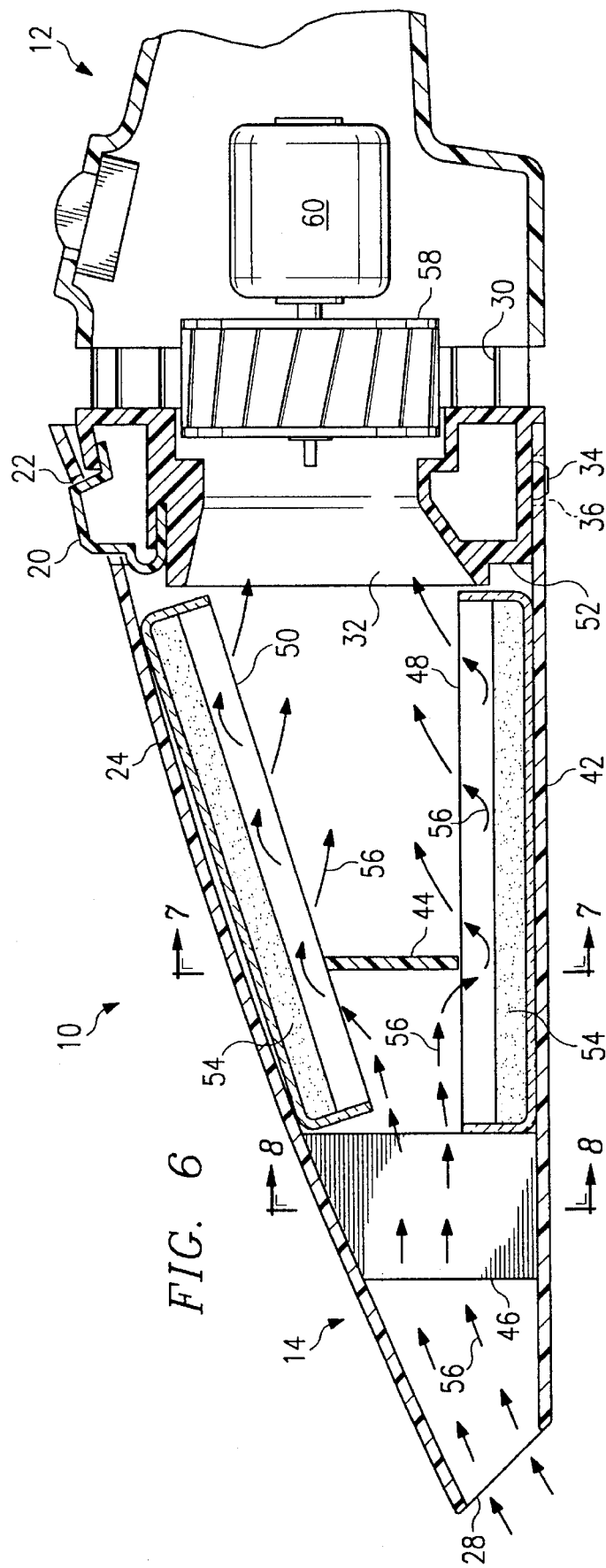
FIG. 6 is a cross-sectional view of the vacuum sampler of FIG. 1 showing the culture dishes mounted and the air flow path from the inlet around the transversely situated air deflector plate and thus onto the culture media and finally to the vacuum inducing fan.

FIG. 6 shows the air inlet 32 of the fan assembly a the front face 52 of tail 12 are spaced apart from an edge of culture dish 48 as well as a similar distance from culture dish 50 to prevent the culture dishes from having any substantial movement in the direction toward tail 12. Shown in the base of the two containers 48 and 50 is nutrient media 54. The open side of each of the containers and thus the nutrient media faces inward. Since the nutrient media is typically in the form of a gelatinous substance such as agar, it will not fall out of the culture dish 50 even though it is upside or open side down.

The plurality of arrows, some of which are labeled 56, represent the air flow path of air traveling through air inlet 28, on both sides of divider stop 46, over the top and under the bottom of deflector 44 and swirling in a turbulent fashion on the right side of aerodynamic deflector 44 before entering the squirrel cage fan 58 powered by motor 60. After the air enters fan 58, it finally exits through outlet openings 30 on the side of tail 12.

It will be observed that the air follows in generally a longitudinal path from nose 28 to fan 58. Further, the deflector 44 is substantially perpendicular or transverse to the overall air flow path. Of prime concern however, is the that the deflector 44 both reduces the overall cross-sectional area of the air path and causes the air to deviate such that it is directed towards the surface of the nutrient media 54 whereby at least some of the microscopic particulates contained therein have a velocity component which is perpendicular to the surface of the nutrient media 54 and many of these microscopic particulates or micro-organisms are caused to embed themselves in the nutrient media where they may grow in a suitable environment. Further, the design of the air enclosure nose 14 and the positioning and size of deflector 44 causes the air downstream of 44 to move in a turbulent manner whereby other particulates still in the air are deposited in downstream portions of containers 48 and 50.

Figure 7:
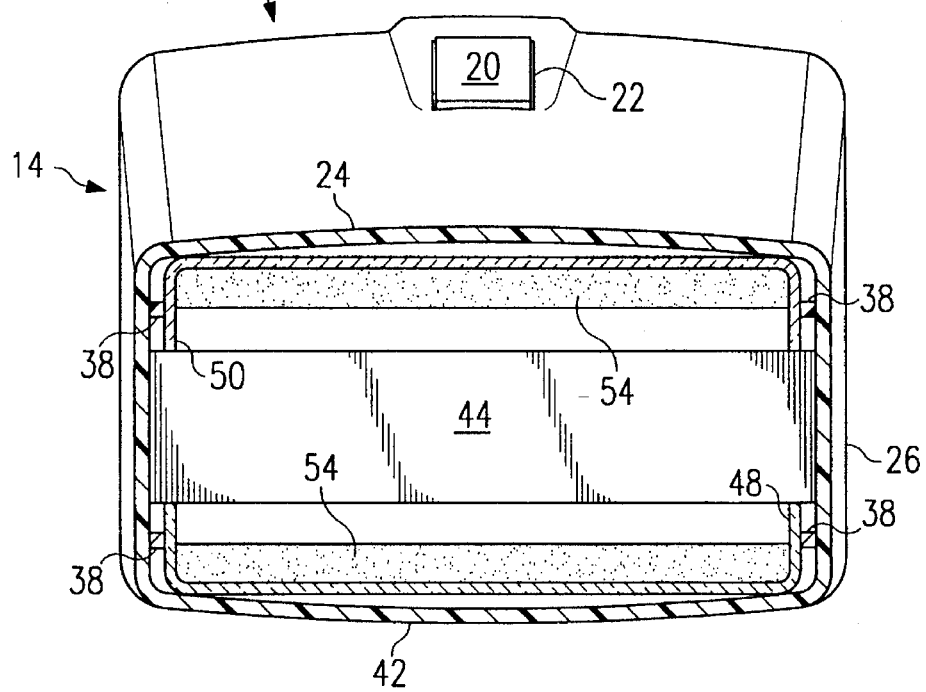
FIG. 7 is a cross-sectional view of the nose portion of FIG. 6 through the air deflector plate as shown in FIG. 6.

FIG. 7 illustrates a cross-sectional view in the area of the deflector plate 44 as shown in FIG. 6. It will be observed that there is nutrient media 54 in each of the culture containers or dishes 48 and 50 and that the open edges of these culture dishes are substantially in contact with deflector plate 44 such that it retains the culture dishes in position. Since there is an air gap between the nutrient material 54 and the edges of the deflector plate, the air is not prevented in its travel from nose 28 to the fan 58. However, since the spacing of the openings between deflector plate 44 and the nutrient material is a much smaller total area than the air intake area at nose 28, there will be a venturi effect to increase the speed of the air at the edge of deflector 44 and will cause a vacuum downstream.

The diversion of the direction of the air combined with the increased speed of the particulates therein initially causes embedding of particulates in the nutrient media 54 before the air expands in the downstream side of deflector plate 44. This air expanding in the vacuum and the positioning of deflector plate 44 will tend to induce the previously mentioned turbulence which causes the contaminates or particulates still remaining in the air to continue to be embedded in portions of nutrient material 54 downstream from deflector plate 44.

Figure 8:
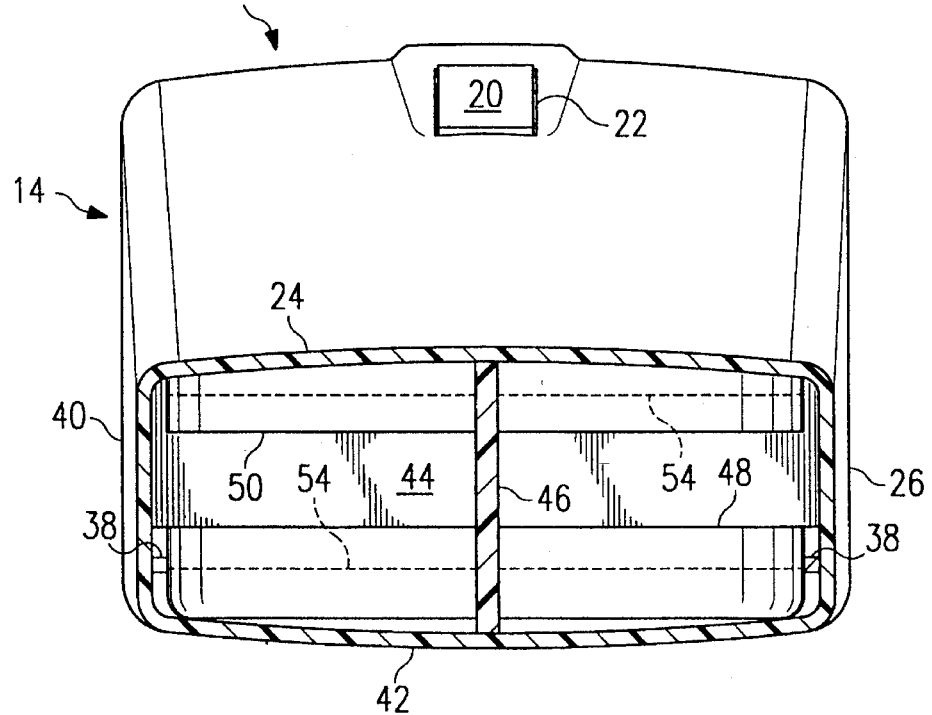
FIG. 8 is a cross-sectional view of the nose portion of FIG. 6 through the divider plate as shown in FIG. 6.

FIG. 8 shows a view of a portion of the nose 14 through the divider plate 46 and as will be observed by comparing FIG. 8 with FIG. 6, only a small portion of culture dish 50 can be seen because of the slope of the top surface 24 of nose 14. Also, the deflector plate 44 because of the angle of the view, is higher than the lower edge of culture dish 50. This also can be observed in FIG. 6. The height of the nutrient media in the dishes 48 and 58 is shown by dash lines.

In summary, the present invention comprises a hand-held portable device, a preferred embodiment of which is illustrated in FIG. 1. This device can be quickly and easily disassembled into two parts as shown in FIGS. 2 and 3 wherein culture dishes such as 48 and 50 can easily be inserted into position as shown in FIG. 5 for sampling the air and the device can be closed to accomplish same. A transverse deflector 44 causes the air drawn into nose 28 to pass over and under deflector 44 and in doing so causes contaminates or microscopic organisms contained in the air to be impacted into the nutrient material 54 due to velocity components in the air which are perpendicular to the nutrient material 54. Further, the venturi effect of the constricted air passage between deflector 44 and nutrient material 54 and the resulting turbulence occurring in the air on the downstream side of the deflector 44 cause further impacts or impactions of the particles in the nutrient material downstream from deflector 44.

Since the fan 58 is downstream from the cultural media, it will not in any way contribute to contamination of subsequent air samples using different nutrient media dishes 48 and 50. The divider 46 and the deflector 44, as well as the rest of the housing of nose 12 is typically made of plastic, thus they are unlikely to hold microscopic organisms that would contaminate future samples. However, if this is a concern, the nose 14 can easily be adapted to remove pieces 44 and 46 such that cleaning materials can be used to sterilize the parts. Further, the entire nose 14 could be dipped in a sterilizing solution or sprayed with an aerosol or trigger sprayer between each air sample without shorting out anything electrical. In any event, the air path for potential contamination from previous air samples is extremely short from nozzle 28 to the nutrient media 54 and contamination is thus unlikely to occur.

Although I have illustrated a preferred embodiment of my inventive concept where batteries would typically be used in the handle 18 of tail 12 to power motor 60 and its associated fan 58 to cause contaminated air to be passed by nutrient material 54, the device could be plugged into an electrical outlet or the fan could be eliminated all together by hooking up to a vacuum source with tubing. The inventive concept is to have a easily detachable air sampling nose such as 14 which contains at least one culture dish such as 48 generally parallel to the overall air path. A deflector plate such as 44 is inserted into the air stream to cause the air particles to directly impinge on the nutrient media and in downstream areas to cause further particles to impinge due to turbulence caused by the deflector plate. I thus wish to be limited not by the scope of the illustrated embodiment but only by the scope of the appended claims.

What is claimed is:

1. Portable sampling apparatus for collecting airborne micro-organisms comprising, in combination:
   an air inlet housing section having top and bottom housing portions and first and second side portions defining a chamber having an anterior inlet port and a posterior vacuum attachment port and having an air flow path therebetween;
   an air deflector plate secured in a fixed position between the first and second side portions of the air inlet housing section, the air deflector plate being spaced from the top and bottom portions and extending across the air flow path, thereby defining first and second separate airflow openings;
   at least one culture dish containing nutrient media disposed within said chamber, said at least one culture dish and nutrient media being disposed generally parallel to the airflow path and upstream of the posterior vacuum attachment port whereby ambient air drawn into the inlet port and through the airflow path flows across the nutrient media before the air exits through the posterior vacuum attachment port; and,
   an outlet housing section releasably coupled to the inlet housing section including air suction apparatus having an airflow impeller for drawing ambient air into the inlet port and through the airflow path and having means for disconnecting and reconnecting the inlet and the outlet housing sections whereby culture dishes located in the inlet housing section may be quickly removed and fresh culture dishes inserted.

2. Portable sampling apparatus for collecting airborne micro-organisms comprising, in combination:
   a culture dish housing having top and bottom housing portions and first and second side portions defining a chamber having an air inlet opening on one end, an air outlet opening at the opposite end and an airflow passable therebetween;
   means for creating a partial vacuum in said chamber including a fan assembly coupled to the air outlet opening;
   at least one culture dish containing nutrient media disposed within said chamber, said culture dish and nutrient media being aligned generally in parallel with overall airflow and upstream relative to said air outlet opening; and,
   an air deflector disposed in said chamber between the top and bottom housing portions, said air deflector being spaced from the top and bottom housing portions, thereby defining first and second air gaps between the deflector and the top and bottom housing portions, respectively.

3. Apparatus as defined in claim 2 comprising, in addition:
   culture dishes, including nutrient media, retained between the air deflector and each of the top and bottom portions.

4. Portable air sampling apparatus which houses removable culture dishes comprising, in combination:
   a vacuum inducing air outlet section having a fan assembly for producing a partial vacuum;
   an air inlet section including a housing defining a chamber having a generally expanding cross-sectional dimension from an anterior end for receiving air to be sampled to a posterior connection end releasably attached to the vacuum inducing air outlet section;
   a culture dish stop located in proximity to the anterior end of the air inlet section;
   at least one culture dish containing nutrient media disposed within said chamber, said culture dish and nutrient media being aligned generally in parallel with the overall airflow through the chamber and upstream relative to the posterior connection end; and,
   an air deflector located downstream from the culture dish stop, the air deflector retaining at least one culture dish against opposing sides of the air inlet section when the vacuum inducing air outlet section is attached to the posterior end of the air inlet section.

5. Sampling apparatus comprising, in combination:
   a detachable air intake nose section and vacuum inducing tail section having an overall air flow path extending generally longitudinally from the nose section to the tail section;
   the air intake nose section having a housing defining a chamber, and the outlet tail section including fan means for creating a partial vacuum within said chamber;
   at least one culture dish containing nutrient media disposed within said chamber, said culture dish and nutrient media being disposed generally parallel to the overall airflow path and upstream relative to the tail section; and,
   an air deflector plate disposed across the overall air flow path in the air intake nose section, an edge of the air deflector plate and an adjacent surface of the nose section creating at least one air flow opening.

6. The sampling apparatus of claim 5 wherein:
   the air deflector plate is situated such that opposite edges of the air deflector plate and adjacent surfaces of the nose section create two air flow openings.

* * * * *